(12) United States Patent
Shibayama et al.

(10) Patent No.: US 9,857,306 B2
(45) Date of Patent: Jan. 2, 2018

(54) SURFACE-ENHANCED RAMAN SCATTERING ELEMENT

(71) Applicant: HAMAMATSU PHOTONICS K.K., Hamamatsu-shi, Shizuoka (JP)

(72) Inventors: Katsumi Shibayama, Hamamatsu (JP); Yoshihiro Maruyama, Hamamatsu (JP); Masashi Ito, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/420,556

(22) PCT Filed: Aug. 9, 2013

(86) PCT No.: PCT/JP2013/071696
§ 371 (c)(1),
(2) Date: Feb. 9, 2015

(87) PCT Pub. No.: WO2014/025027
PCT Pub. Date: Feb. 13, 2014

(65) Prior Publication Data
US 2015/0233833 A1    Aug. 20, 2015

(30) Foreign Application Priority Data

Aug. 10, 2012  (JP) ................. 2012-178773

(51) Int. Cl.
*G01N 21/65* (2006.01)

(52) U.S. Cl.
CPC ..... *G01N 21/658* (2013.01); *G01N 2021/651* (2013.01)

(58) Field of Classification Search
CPC .................................................... G01N 21/658
See application file for complete search history.

(56) References Cited

U.S. PATENT DOCUMENTS

| | | |
|---|---|---|
| 9,127,984 B2 * | 9/2015 | Tseng .................. G01N 21/658 |
| 2004/0023046 A1 | 2/2004 | Schlottig et al. |
| 2006/0146323 A1 | 7/2006 | Bratkovski et al. |
| 2008/0094621 A1 | 4/2008 | Li et al. |

(Continued)

FOREIGN PATENT DOCUMENTS

| | | |
|---|---|---|
| CN | 101057132 | 10/2007 |
| CN | 101221435 | 7/2008 |

(Continued)

OTHER PUBLICATIONS

"Q-SERS™ G1 Substrate," Opto Science, Inc. (retrieved on-line on Jul. 5, 2013).
Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

(Continued)

*Primary Examiner* — Shawn Decenzo
(74) *Attorney, Agent, or Firm* — Drinker Biddle & Reath LLP

(57) ABSTRACT

A SERS element comprises a substrate; a fine structure part formed on a front face of the substrate and having a plurality of pillars; and a conductor layer formed on the fine structure part and constituting an optical function part for generating surface-enhanced Raman scattering. The pillars have respective side faces provided with grooves. A plurality of gaps are formed in the conductor layer by entering the grooves.

10 Claims, 19 Drawing Sheets

(56) References Cited

U.S. PATENT DOCUMENTS

| | | | |
|---|---|---|---|
| 2008/0218761 | A1 | 9/2008 | Nishikawa et al. |
| 2008/0297802 | A1 | 12/2008 | Ogawa et al. |
| 2011/0027901 | A1 | 2/2011 | Gaster et al. |
| 2011/0116089 | A1 | 5/2011 | Schmidt et al. |
| 2011/0166045 | A1 | 7/2011 | Dhawan et al. |
| 2012/0170033 | A1* | 7/2012 | Zhu .............. G01N 21/658 356/301 |
| 2014/0043605 | A1 | 2/2014 | Tseng et al. |
| 2016/0146736 | A1* | 5/2016 | Chen .............. G01N 21/658 356/301 |

FOREIGN PATENT DOCUMENTS

| | | |
|---|---|---|
| CN | 101281133 | 10/2008 |
| CN | 101319994 | 12/2008 |
| CN | 101408513 | 4/2009 |
| CN | 101460830 | 6/2009 |
| CN | 102103086 | 6/2011 |
| CN | 102169088 | 8/2011 |
| CN | 102282094 | 12/2011 |
| CN | 102483354 | 5/2012 |
| CN | 102483866 | 5/2012 |
| GB | 2419940 | 5/2006 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO 2011/121857 | 10/2011 |
| WO | WO-2012/024006 A2 | 2/2012 |
| WO | WO 2013/015810 | 1/2013 |
| WO | WO-2014/025033 A1 | 2/2014 |
| WO | WO-2014/025034 A1 | 2/2014 |

OTHER PUBLICATIONS

International Search Report dated Nov. 12, 2013, issued in International Application No. PCT/JP2013/071695.
International Search Report dated Nov. 5, 2013, issued in International Application No. PCT/JP2013/071696.
International Search Report dated Nov. 5, 2013, issued in International Application No. PCT/JP2013/071700.
International Search Report dated Nov. 19, 2013, issued in International Application No. PCT/JP2013/071702.
International Search Report dated Nov. 12, 2013, issued in International Application No. PCT/JP2013/071703.
International Search Report dated Nov. 5, 2013, issued in International Application No. PCT/JP2013/071709.
International Search Report dated Nov. 5, 2013, issued in International Application No. PCT/JP2013/071710.
International Search Report dated Apr. 28, 2014, issued in International Application No. PCT/JP2014/052926.
International Search Report dated May 13, 2014, issued in International Application No. PCT/JP2014/052928.
W. Zhang et al., "Giant and uniform fluorescence enhancement over large areas using plamonic nanodots in 3D resonant cavity nanoantenna by nanoimprinting", Nanotechnolgy, vol. 23, No, 22, May 10, 2012, p. 225301, XP020224099.
S. M. Wells et al., "Efficient disc on pillar substrates for surface enhanced Raman spectroscopy", Chemical Communications—Chemcom, vol. 47, No. 13, Jan. 1, 2011, p. 3814-p. 3816, XP055289549.
U.S. Office Action dated Oct. 14, 2016 that issued in U.S. Appl. No. 14/420,510 including Double Patenting Rejections on pp. 2-14.
English Machine Translation of JP 2011-107032, Nishikawa et al., dated Jun. 2, 2011 as attached to U.S. Office Action dated Oct. 14, 2016 in U.S. Appl. No. 14/420,510.
Wei Fen Jiang et al., "Improved surface-enhanced Raman scattering of patterned gold nanoparticles deposited in silicon nanoporous pillar arrays", Applied Surface Science, vol. 257, No. 18, Apr. 25, 2011, p. 8089-p. 8092, XP028373693.
Su Yeon Lee, et al., "Freestanding and Arrayed Nanoporous Microcylinders for Highly Active 3D SERS Substrate", Chemistry of Materials, vol. 25, No. 12, Jun. 25, 2013, p. 2421-p. 2426, XP55286875.
K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.
M. Tomohiko et al., "New localized surface plasmon resonance sensor utilizing nanoimprinting technology", NSTI Nanotechnology Conference and Trade Show—NSTI Nanotech, vol. 1, May 11, 2006, p. 58-p. 61, XP009098538.
W. D. Li et al., "Three-dimensional cavity nanoantenna coupled plasmonic nanodots for ultrahigh and uniform surface-enhanced Raman scattering over large area", Optics Express, vol. 19, No, 5, Feb. 14, 2011, p. 3925-3936, XP002751299.

* cited by examiner

*Fig.6*
(a)
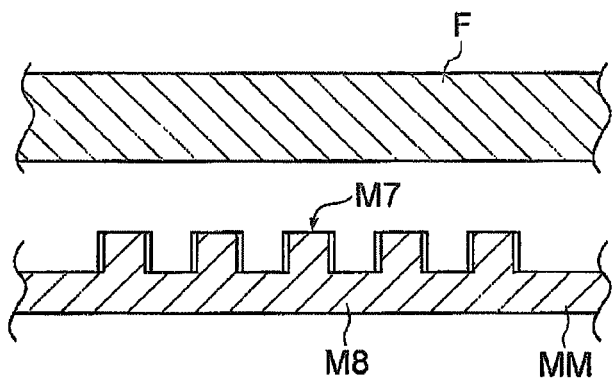
(b)
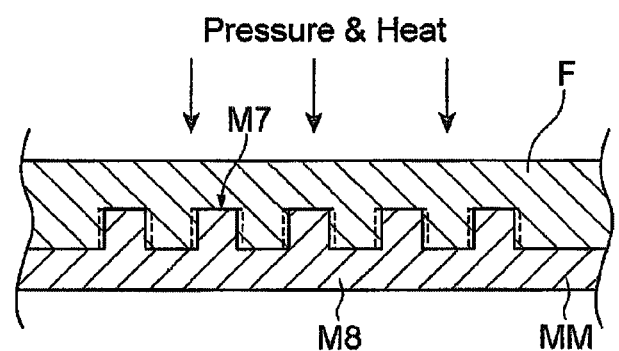
(c)
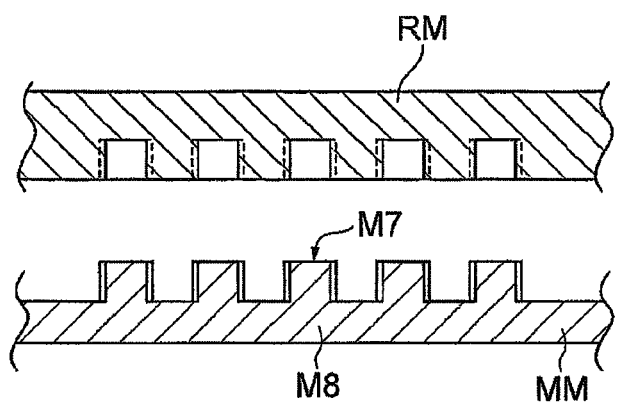

Fig.7
(a)
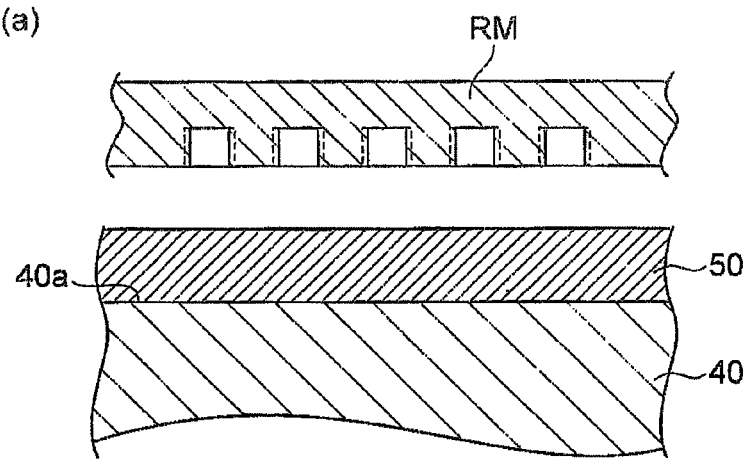
(b)
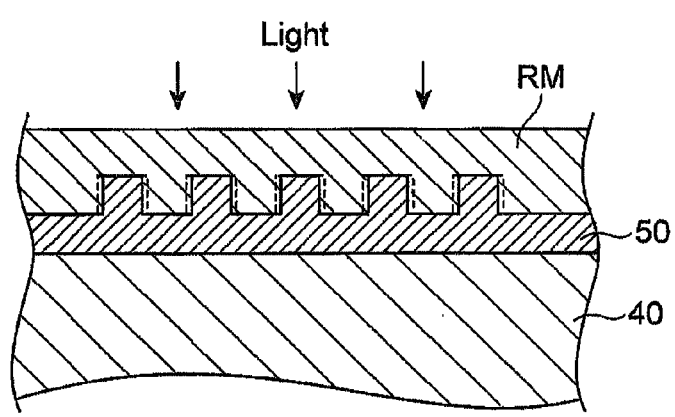
(c)
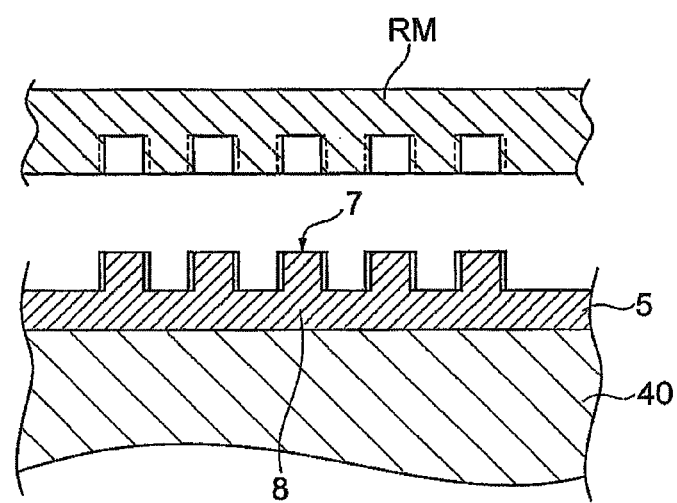

Fig. 10
(a)
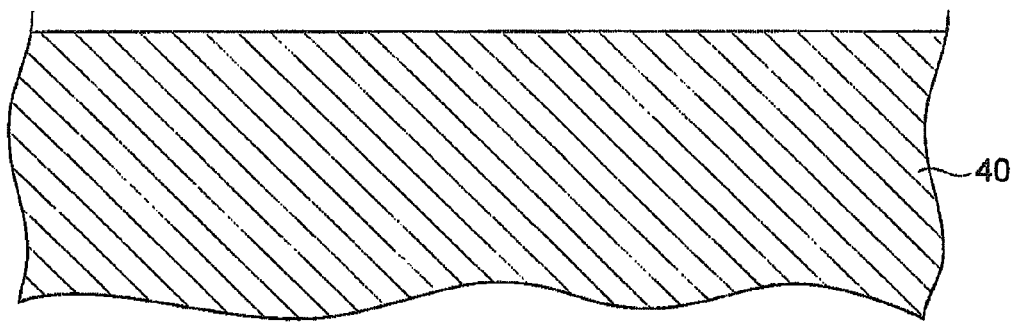
(b)
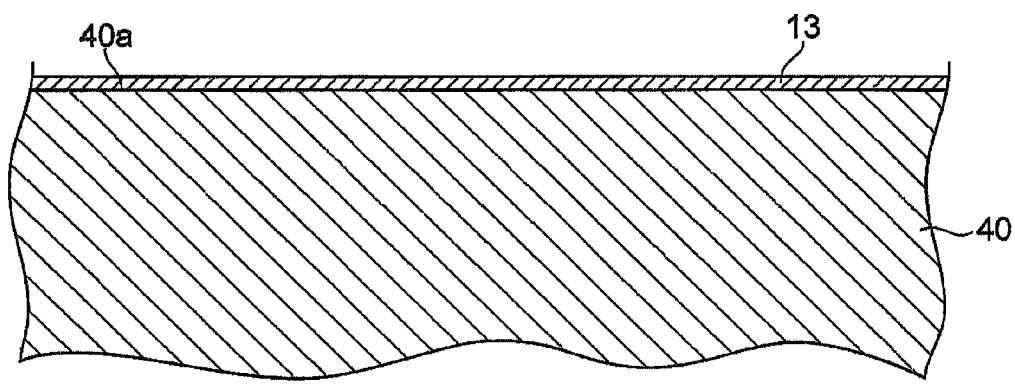
(c)
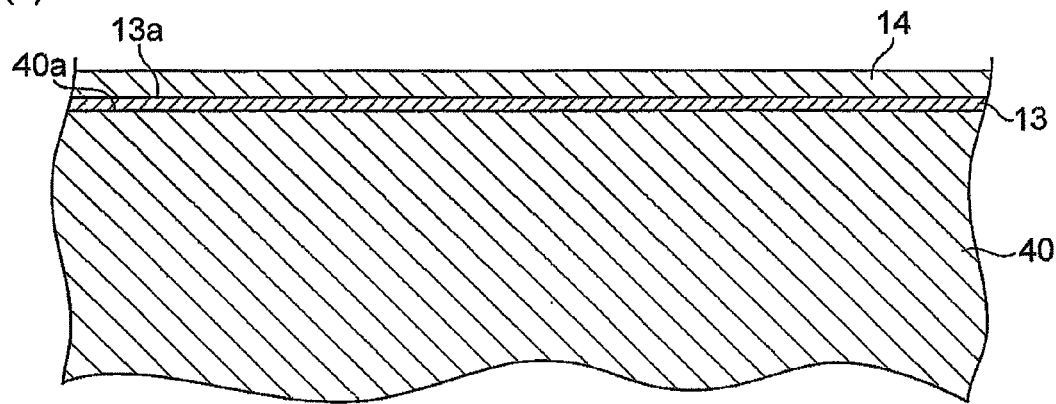

Fig.11
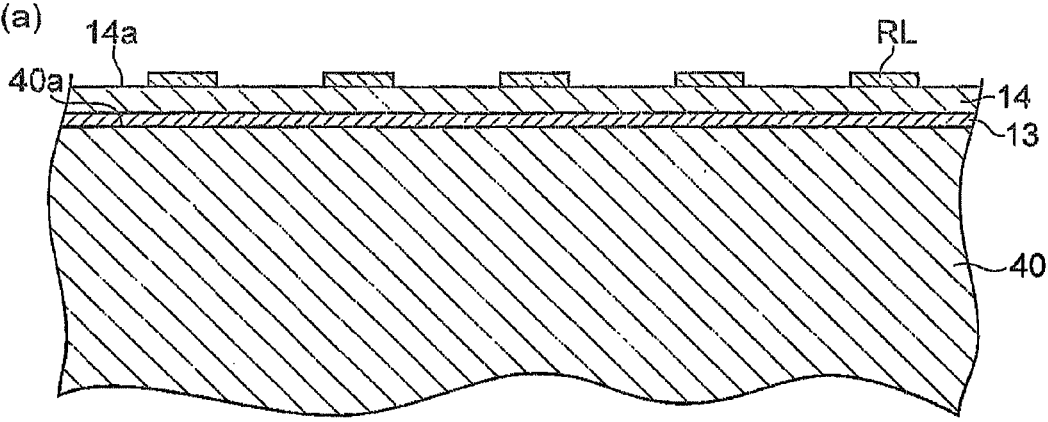
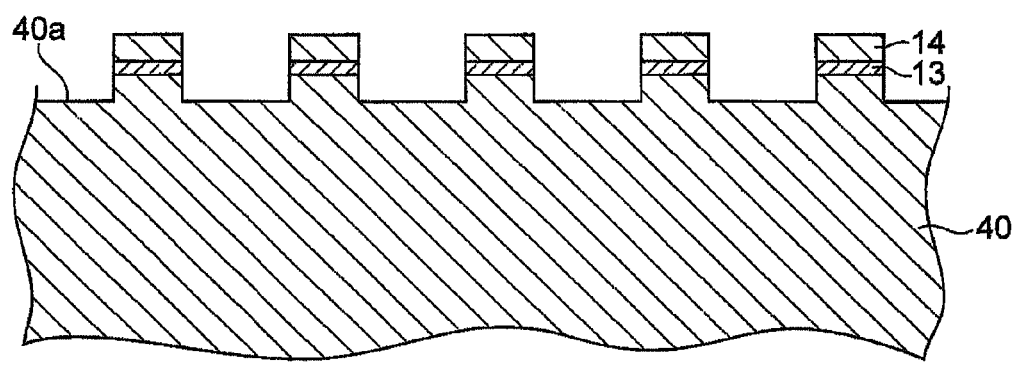
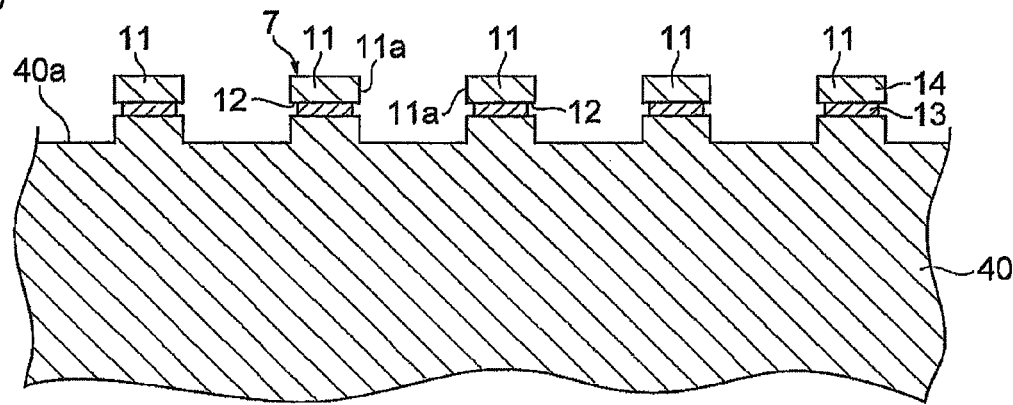

SURFACE-ENHANCED RAMAN SCATTERING ELEMENT

TECHNICAL FIELD

The present invention relates to a surface-enhanced Raman scattering element.

BACKGROUND ART

As a conventional surface-enhanced Raman scattering element, one equipped with a minute metal structure configured to generate surface-enhanced Raman scattering (SERS) has been known (see, for example, Patent Literature 1 and Non Patent Literature 1), in such a surface-enhanced Raman scattering element, when a sample to be subjected to Raman spectroscopic analysis is brought into contact with the minute metal structure and is irradiated with excitation light in this state, surface-enhanced Raman scattering occurs, whereby Raman scattering light enhanced by about $10^8$ times, for example, is released.

Meanwhile, for example, Patent Literature 2 discloses a minute metal structure in which metal layers are formed on one surface of a substrate and upper surfaces of a plurality of minute projections formed on the one surface of the substrate (or bottom faces of a plurality of fine holes formed on the one surface of the substrate) so as to be out of contact with each other (such that the shortest distance therebetween is on the order of 5 nm to 10 μm).

CITATION LIST

Patent Literature

Patent Literature 1: Japanese Patent Application Laid-Open No. 2011-33518
Patent Literature 2: Japanese Patent Application Laid-Open No. 2009-222507

Non Patent Literature

Non Patent Literature 1: "Q-SERS™ G1 Substrate", [online], Opto Science, Inc., [retrieved from the Internet on 2012 Jul. 19].

SUMMARY OF INVENTION

Technical Problem

When a minute metal structure is formed with a so-called nanogap as mentioned above, electric fields are locally enhanced upon irradiation with excitation light, whereby the intensity of surface-enhanced Raman scattering increases.

It is therefore an object of the present invention to provide a surface-enhanced Raman scattering element which can increase the intensity of surface-enhanced Raman scattering by a favorable nanogap.

Solution to Problem

The surface-enhanced Raman scattering element in accordance with one aspect of the present invention comprises a substrate having a principal surface; a fine structure part formed on the principal surface and having a plurality of projections; and a conductor layer formed on the fine structure part and constituting an optical function part for generating surface-enhanced Raman scattering; the projections having respective outer surfaces provided with recessed regions; a plurality of gaps being formed in the conductor layer by entering the recessed regions.

In this surface-enhanced Raman scattering element, the conductor layer enters the recessed regions provided in the respective outer surfaces of the projections of the fine structure part, thereby forming a plurality of gaps in the conductor layer constituting the optical function part. The gaps formed in the conductor layer favorably function as nanogaps where electric fields are locally enhanced. Therefore, this surface-enhanced Raman scattering element can increase the intensity of surface-enhanced Raman scattering by favorable nanogaps.

In the surface-enhanced Raman scattering element in accordance with one aspect of the present invention, the projections may be arranged periodically along the principal surface. This configuration can stably increase the intensity of surface-enhanced Raman scattering.

In the surface-enhanced Raman scattering element in accordance with one aspect of the present invention, one projection may be provided with a plurality of recessed regions. This configuration can increase gaps which favorably function as nanogaps.

In the surface-enhanced Raman scattering element in accordance with one aspect of the present invention, the recessed region may be a groove extending along a center line of the projection or a groove extending so as to surround the center line of the projection. Each of these configurations enables the gap formed at a position corresponding to the recessed region to function favorably as a nanogap.

The surface-enhanced Raman scattering element in accordance with one aspect of the present invention comprises a substrate having a principal surface; a fine structure part formed on the principal surface and having a plurality of depressions; and a conductor layer formed on the fine structure part and constituting an optical function part for generating surface-enhanced Raman scattering; the depressions having respective inner surfaces provided with recessed regions; a plurality of gaps being formed in the conductor layer by entering the recessed regions.

In this surface-enhanced Raman scattering element, the conductor layer enters the recessed regions provided in the respective inner surfaces of the depressions of the fine structure part, thereby forming a plurality of gaps in the conductor layer constituting the optical function part. The gaps formed in the conductor layer favorably function as nanogaps where electric fields are locally enhanced. Therefore, this surface-enhanced Raman scattering element can increase the intensity of surface-enhanced Raman scattering by favorable nanogaps.

In the surface-enhanced Raman scattering element in accordance with one aspect of the present invention, the depressions may be arranged periodically along the principal surface. This configuration can stably increase the intensity of surface-enhanced Raman scattering.

In the surface-enhanced Raman scattering element in accordance with one aspect of the present invention, one depression may be provided with a plurality of recessed regions. This configuration can increase gaps which favorably function as nanogaps.

In the surface-enhanced Raman scattering element in accordance with one aspect of the present invention, the recessed region may be a groove extending along a center line of the depression or a groove extending so as to surround the center line of the depression. Each of these configurations enables the gap formed at a position corresponding to the recessed region to function favorably as a nanogap.

Advantageous Effects of Invention

The present invention can provide a surface-enhanced Raman scattering element which can increase the intensity of surface-enhanced Raman scattering by a favorable nanogap.

BRIEF DESCRIPTION OF DRAWINGS

FIG. 6 is a sectional view illustrating steps of manufacturing the surface-enhanced Raman scattering element of FIG. 1;

FIG. 7 is a sectional view illustrating steps of manufacturing the surface-enhanced Raman scattering element of FIG. 1;

FIG. 10 is a sectional view illustrating steps of manufacturing the surface-enhanced Raman scattering element in accordance with the second embodiment of the present invention;

FIG. 11 is a sectional view illustrating steps of manufacturing the surface-enhanced Raman scattering element in accordance with the second embodiment of the present invention;

DESCRIPTION OF EMBODIMENTS

Figure 1:
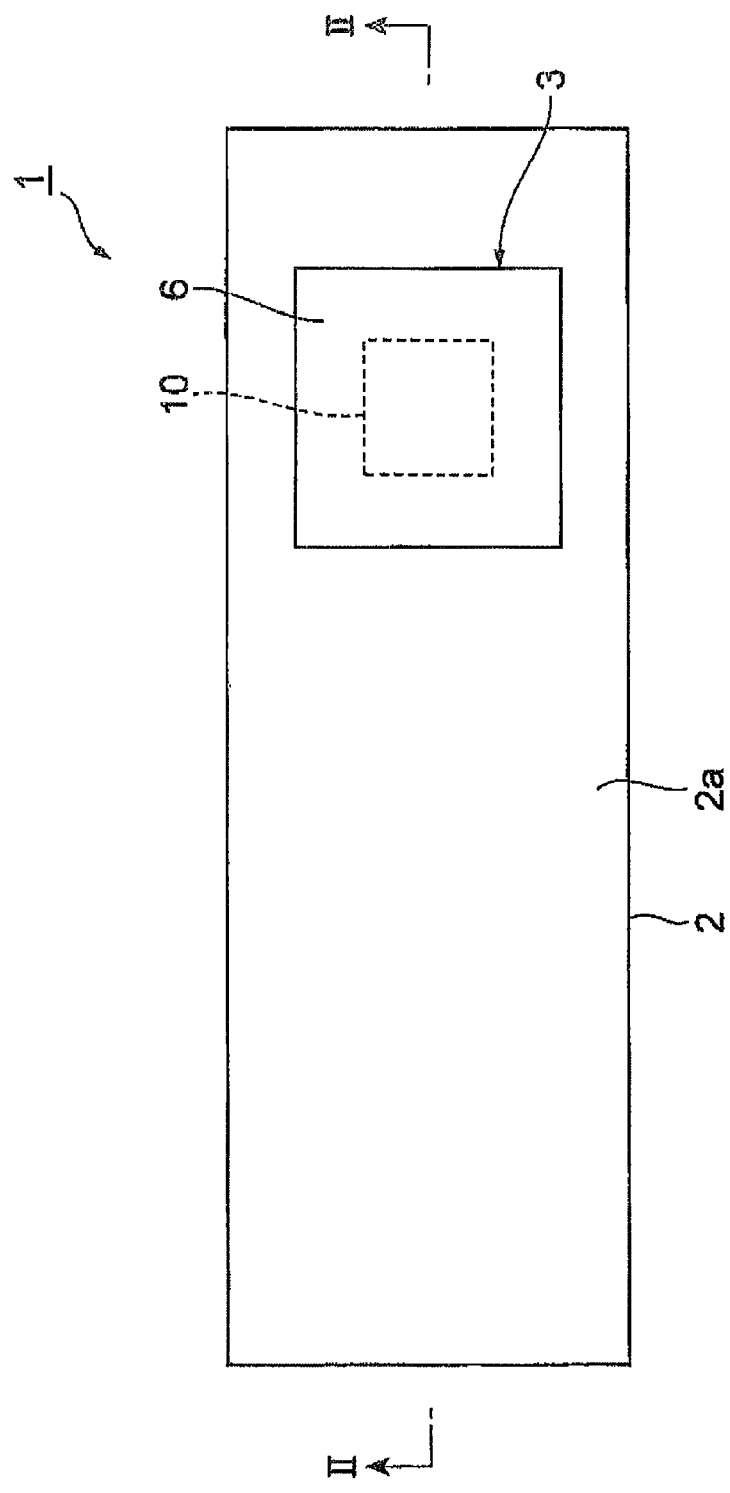
FIG. 1 is a plan view of a surface-enhanced Raman scattering unit equipped with a surface-enhanced Raman scattering element in accordance with a first embodiment of the present invention.

In the following, preferred embodiments of the present invention will be explained in detail with reference to the drawings. In the drawings, the same or equivalent parts will be referred to with the same signs while omitting their overlapping descriptions.

First Embodiment

Figure 2:
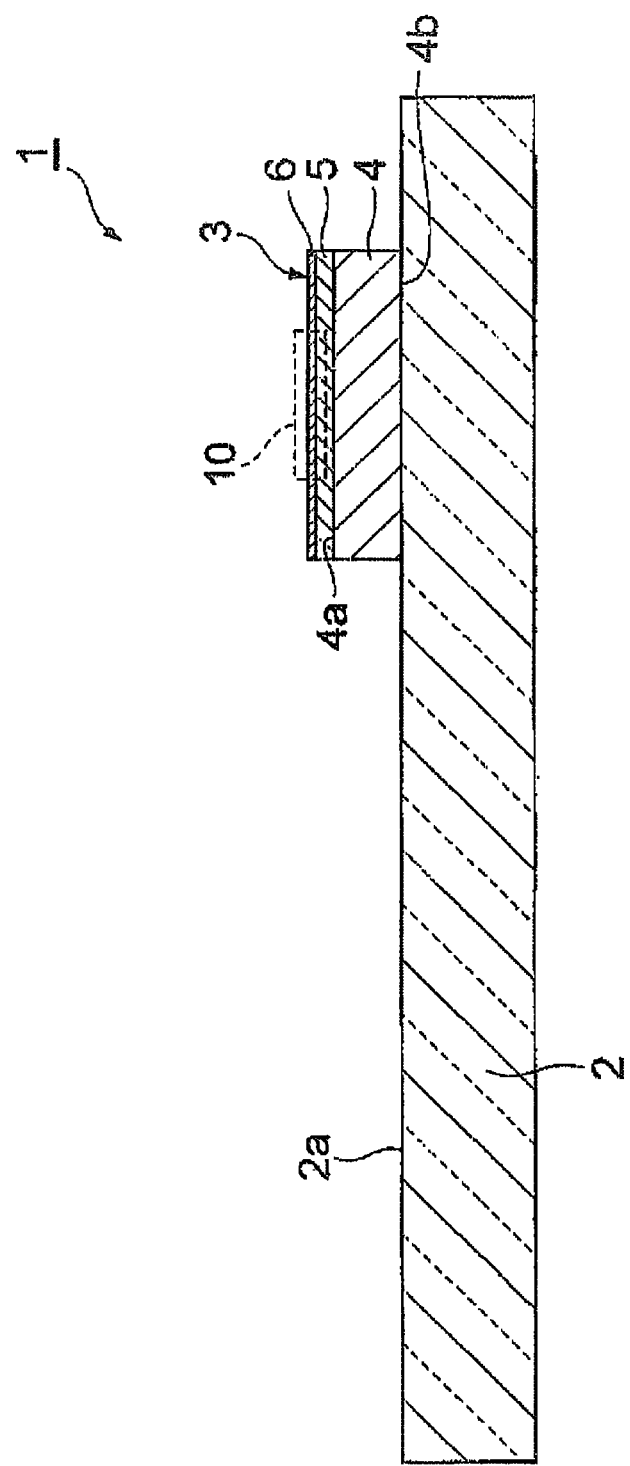
FIG. 2 is a sectional view taken along the line II-II of FIG. 1.

As illustrated in FIGS. 1 and 2, a SERS unit (surface-enhanced Raman scattering unit) 1 in accordance with the first embodiment comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one end part in the longitudinal direction of the handling board 2.

The SERS element 3 comprises a substrate 4 attached onto the handling board 2, a molded layer 5 formed on the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
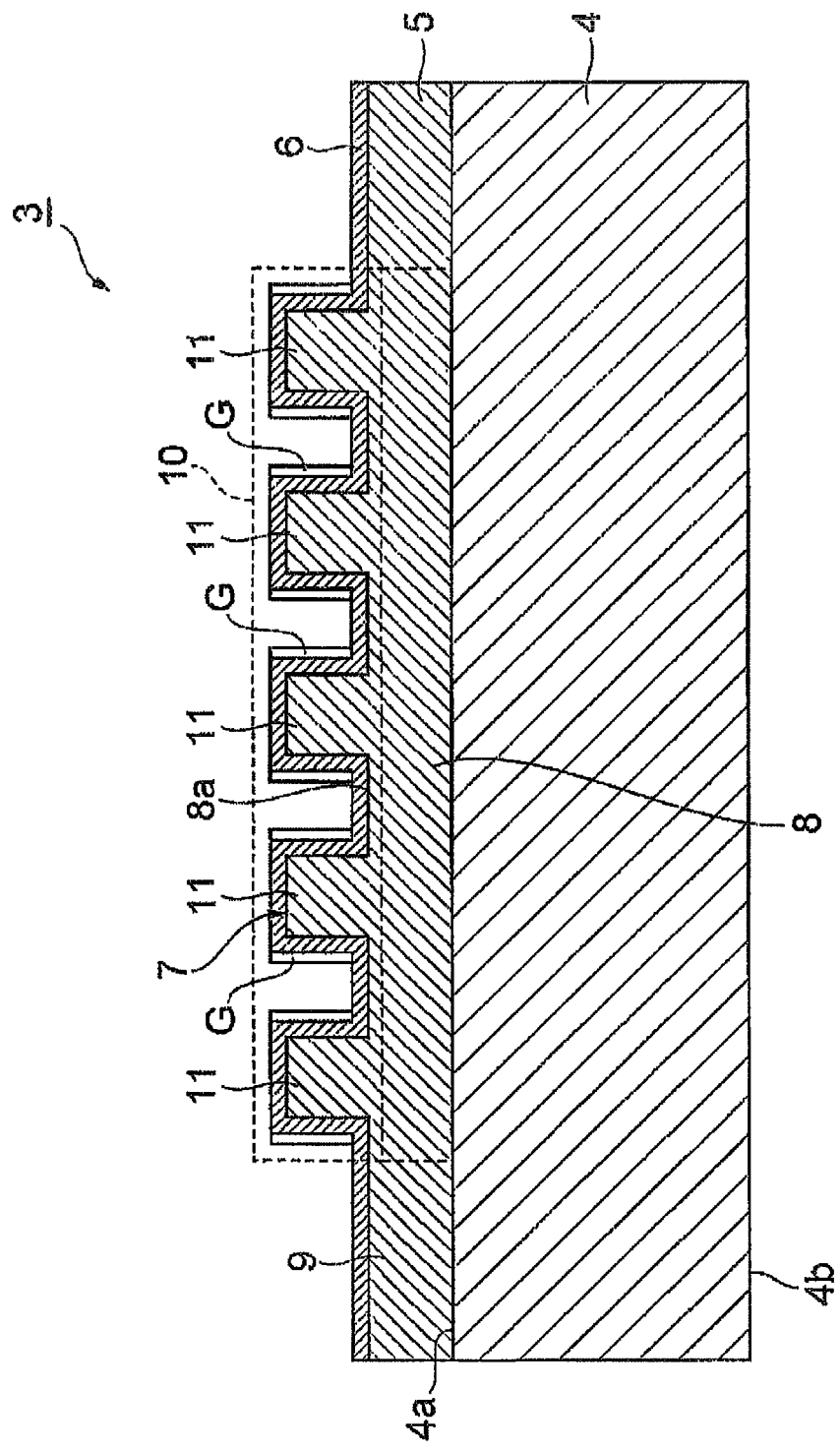
FIG. 3 is a vertical sectional view of an optical function part in the surface-enhanced Raman scattering element of FIG. 1.

As illustrated in FIG. 3, the molded layer 5 includes a fine structure part 7, a support part 8, and a frame part 9. The fine structure part 7, which is a region having a periodic pattern, is formed on a surface layer on the side opposite from the substrate 4 at a center part of the molded layer 5. In the fine structure part 7, a plurality of circular columnar pillars (projections) 11, each having a diameter and height on the order of several nm to several hundred nm, are periodically arranged at a pitch on the order of several ten nm to several hundred nm (preferably 250 nm to 800 nm) along a front face (principal surface) 4a of the substrate 4. The fine structure part 7 has a rectangular outer form on the order of several hundred μm×several hundred μm to several ten mm×several ten mm when seen in the thickness direction of the substrate 4. The support part 8, which is a rectangular region supporting the fine structure part 7, is formed on the front face 4a of the substrate 4. The frame part 9, which is a rectangular ring-shaped region surrounding the support part 8, is formed on the front face 4a of the substrate 4. The support part 8 and frame part 9 have a thickness on the order of several ten nm to several ten μm. The molded layer 5 like this is integrally formed by molding a resin (examples of which include resins based on acrylics, fluorine, epoxy, silicone, and urethane, PET, polycarbonate, and inorganic/organic hybrid materials) or low-melting glass arranged on the substrate 4 by nanoimprinting, for example.

The conductor layer 6 is formed over the fine structure part 7 and frame part 9. In the fine structure part 7, the conductor layer 6 reaches a surface 8a of the support part 8 which is exposed to the side opposite from the substrate 4. The conductor layer 6 has a thickness on the order of several nm to several μm. The conductor layer 6 like this is formed by vapor-depositing a conductor such as a metal (Au, Ag, Al, Cu, Pt, or the like) on the molded layer 5 molded by nanoimprinting, for example. In the SERS element 3, the conductor layer 6 formed on the fine structure part 7 and the surface 8a of the support part 8 constructs an optical function part 10 which generates surface-enhanced Raman scattering.

Figure 4:
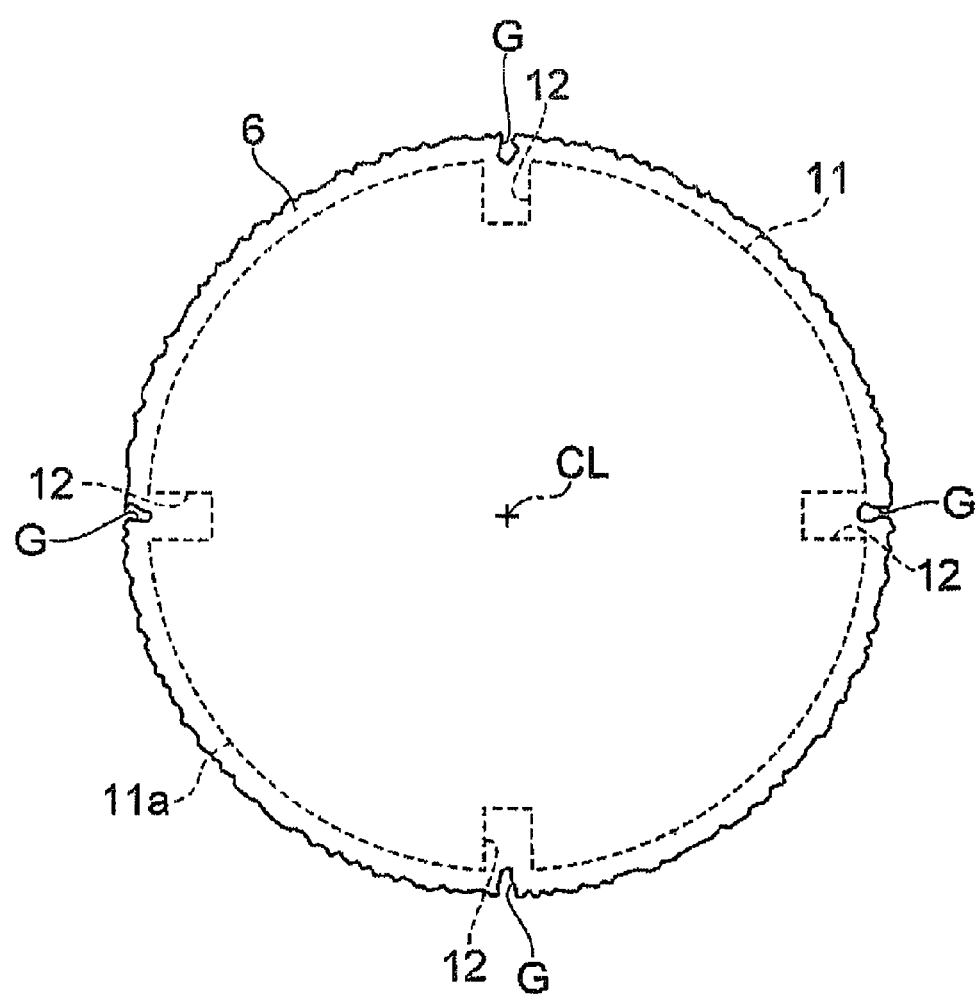
FIG. 4 is a plan view of a pillar and conductor layer in the optical function part of FIG. 3.
Figure 5:
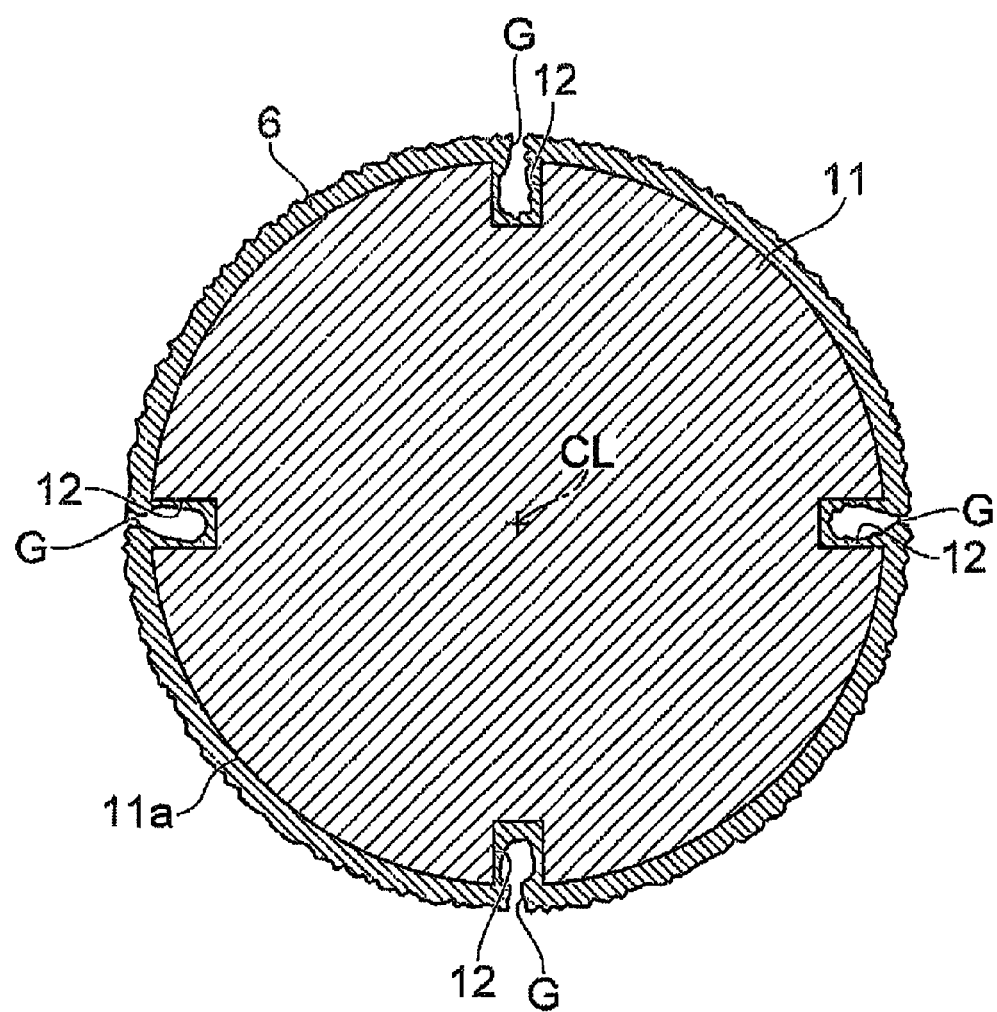
FIG. 5 is a horizontal sectional view of the pillar and conductor layer in the optical function part of FIG. 3.

As illustrated in FIGS. 4 and 5, each pillar 11 has a side face (outer surface) 11a provided with grooves (recessed regions) 12, each of which has a rectangular cross section. One pillar 11 is provided with a plurality of grooves 12 (four grooves at intervals of 90 degrees about a center line CL of the pillar 11 in the SERS element 3 of the first embodiment), each of which extends along the center line CL. Each groove 12 has a width and depth on the order of several nm to several ten nm. The conductor layer 6 is formed on the outer surfaces of the pillars 11 and enters the respective grooves 12 in the side face 11a of each pillar 11. As a consequence, the conductor layer 6, which constitutes the optical function part 10, is formed with gaps G along the respective grooves 12. The gaps G have intervals on the order of 0 to several ten nm. The center line CL of the pillar 11 is a line passing through the respective centers of gravity in cross-sectional forms of the pillar 11 which are perpendicular to the center line CL.

The SERS unit 1 constructed as in the foregoing is used as follows. First, a ring-shaped spacer made of silicone, for example, is arranged on the front face 2a of the handling board 2 so as to surround the SERS element 3. Subsequently, a sample of a solution (or a dispersion of a powder sample in a solution such as water or ethanol) is dropped to the inside of the spacer with a pipette or the like, so as to arrange the sample on the optical function part 10. Then, for reducing the lens effect, a glass cover is mounted on the spacer and brought into close contact with the solution sample.

Next, the SERS unit 1 is set in a Raman spectroscopic analyzer, and the sample arranged on the optical function part 10 is irradiated with excitation light through the glass cover. This generates surface-enhanced Raman scattering at the interface between the optical function part 10 and sample, whereby surface-enhanced Raman scattering light derived from the sample is enhanced by about $10^8$ times, for example, and released. Hence, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10.

In the SERS element 3 of the first embodiment, as explained in the foregoing, the conductor layer 6 enters the grooves 12 provided in the side faces 11a of the pillars 11 in the fine structure part 7, thereby forming a plurality of gaps G in the conductor layer 6 constituting the optical function part 10. The gaps G formed in the conductor layer 6 favorably function as nanogaps where electric fields are locally enhanced. Therefore, the SERS element 3 of the first embodiment can increase the intensity of surface-enhanced Raman scattering by favorable nanogaps.

Since a plurality of pillars 11 are periodically arranged along the front face 4a of the substrate 4, the intensity of surface-enhanced Raman scattering can be increased stably.

Since one pillar 11 is provided with a plurality of grooves 12, the gaps G favorably functioning as nanogaps can be increased.

An example of methods for manufacturing the SERS element 3 in accordance with the first embodiment will now be explained. First, as illustrated in (a) of FIG. 6, a master mold MM and a film base F are prepared. The master mold MM includes a fine structure part M7 corresponding to the fine structure part 7 and a support part M8 for supporting the fine structure part M7. A plurality of fine structure parts M7 are arranged in a matrix on the support part M8. Subsequently, as illustrated in (b) of FIG. 6, the film base F is pressed against the master mold MM and pressurized and heated in this state, so as to transfer a pattern of the plurality of fine structure parts M7 to the film base F. Then, as illustrated in (c) of FIG. 6, the film base F is released from the master mold MM, so as to yield a replica mold (replica film) RM having the pattern of the plurality of fine structure parts M7 transferred thereto. The replica mold RM may also be one formed by applying a resin (examples of which include resins based on epoxy, acrylics, fluorine, silicone, and urethane and inorganic/organic hybrid resins) onto the film base F. When the resin to be applied onto the film base F is UV-curable, the replica mold R can be obtained by curing the resin applied on the film base F by irradiation with UV (UV nanoimprinting) instead of thermal nanoimprinting.

Next, as illustrated in (a) of FIG. 7, a silicone wafer 40 to become the substrate 4 is prepared, and a UV-curable resin is applied onto a front face 40a of the silicon wafer 40, so as to form a nanoimprinting layer 50 to become the molded layer 5 on the silicone wafer 40. Subsequently, as illustrated in (b) of FIG. 7, the replica mold RM is pressed against the nanoimprinting layer 50, and the nanoimprinting layer 50 is irradiated with UV in this state, so as to be cured, whereby the pattern of the replica mold RM is transferred to the nanoimprinting layer 50. Then, as illustrated in (c) of FIG. 7, the replica mold R is released from the nanoimprinting layer 50, so as to yield the silicone wafer 40 formed with a plurality of fine structure parts 7. For securely curing the resin, thermal cure may be performed.

Next, a film of a metal such as Au or Ag is produced on the molded layer 5 by vapor deposition such as resistance heating vapor deposition and electron beam vapor deposition or sputtering, so as to form the conductor layer 6. At this time, the conductor layer 6 enters the grooves 12 provided in the side faces 11a of the pillars 11 in the fine structure part 7, thereby forming the gaps G in the conductor layer 6 constituting the optical function part 10. Subsequently, the silicone wafer 40 is cut for each fine structure part 7 (i.e., for each optical function part 10), whereby a plurality of SERS elements 3 are obtained. For yielding the SERS unit 1, it is sufficient for the SERS element 3 manufactured as mentioned above to be attached onto the handling board 2.

For forming the conductor layer 6, planetary vapor deposition which performs vapor deposition on a plurality of silicon wafers 40 set to a planetary member revolving and rotating with respect to a vapor deposition source is effective. As compared with vapor deposition techniques of opposed type and rotating dome types, the planetary vapor deposition can produce the conductor layer 6 more uniformly on the side faces 11a of the pillars 11, thereby more stably forming the gaps G in the conductor layer 6 constituting the optical function part 10.

Sputtering is also effective for forming the conductor layer 6. The sputtering causes metal particles to adhere to the molded layer 5 while colliding with each other due to plasma discharge, thereby randomizing their directivity, so that the metal particles wrap around well to the side faces 11a of the pillars 11. Therefore, the sputtering can also produce the conductor layer 6 uniformly on the side faces 11a of the pillars 11, thereby stably forming the gaps G in the conductor layer 6 constituting the optical function part 10.

As explained in the foregoing, the method for manufacturing the SERS element 3 in accordance with the first embodiment forms a plurality of gaps G in the conductor layer 6 by utilizing the grooves 12 provided in the side face 11a of each pillar 11. This can yield the gaps G, which favorably function as nanogaps, more stably than in the case of forming the gaps G at root parts of the pillars 11 where the forming condition of the conductor layer 6 is hard to stabilize.

Simply transferring a pattern of a two-dimensional form of the replica mold RM can form the grooves 12 extending along the center line CL of the pillar 11 on the side face 11a of the pillar 11. The pattern of the two-dimensional form can easily be changed in the replica mold RM, whereby the SERS element 3 formed with favorable nanogaps which can increase the intensity of surface-enhanced Raman scattering can be manufactured with a favorable yield.

Not only the above-mentioned UV nanoimprinting, but thermal nanoimprinting can also be used as nanoimprinting. Nickel, silicon, or the like can be used as a mold material for thermal nanoimprinting.

In place of the above-mentioned nanoimprinting, a mask having a pattern in a two-dimensional form may be formed by photoetching, electron beam lithography, or the like, and the fine structure part 7 may be formed on the substrate 4 by etching with this mask. The pattern of the two-dimensional form is also easily changeable in the mask in this case, whereby the SERS element 3 formed with favorable nanogaps which can increase the intensity of surface-enhanced Raman scattering can be manufactured with a favorable yield.

Second Embodiment

Figure 8:
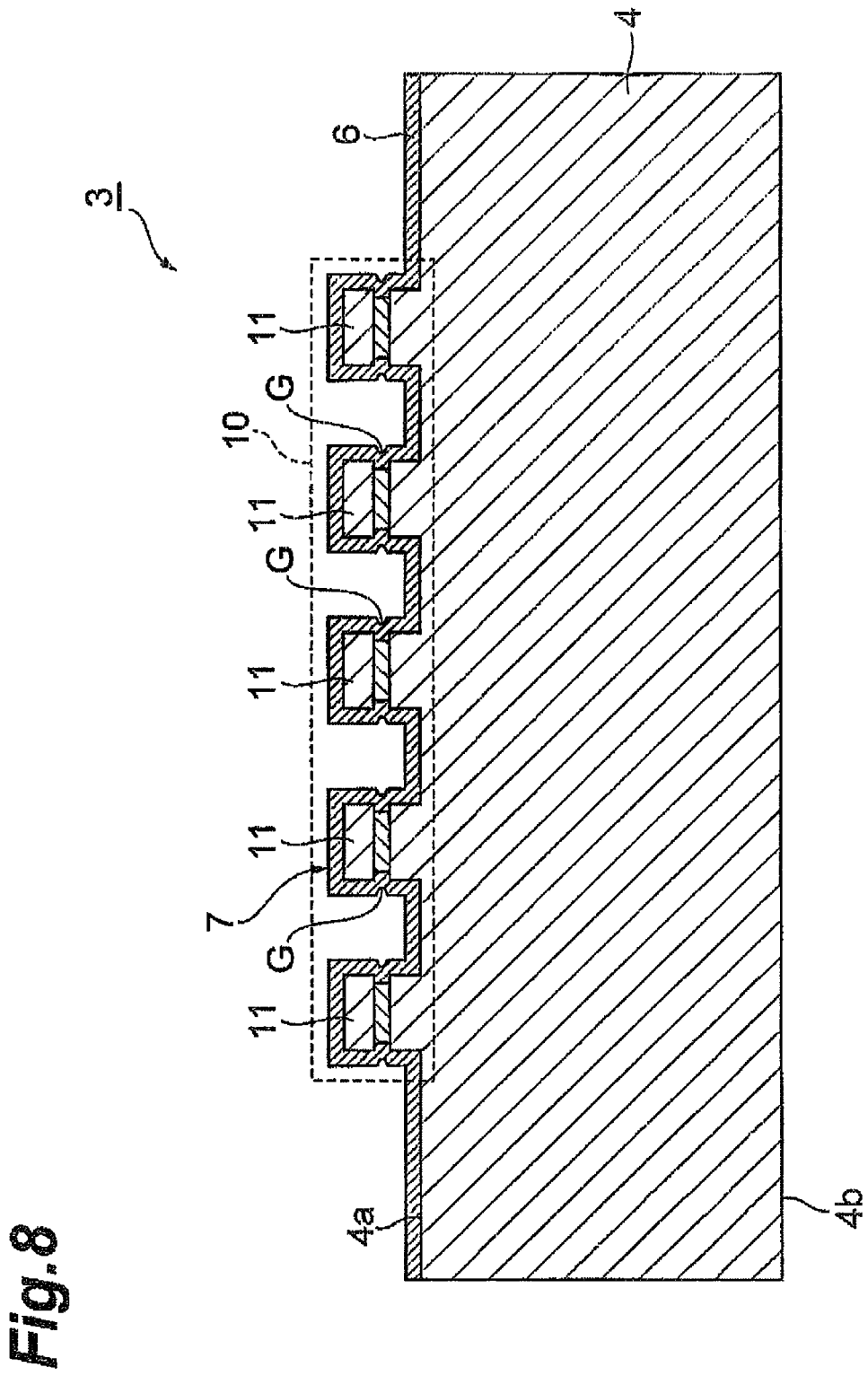
FIG. 8 is a vertical sectional view of the optical function part in the surface-enhanced Raman scattering element in accordance with a second embodiment of the present invention.

As illustrated in FIG. 8, the SERS element 3 of the second embodiment differs from the above-mentioned SERS element 3 of the first embodiment mainly in that the fine structure part 7 is formed on the front face 4a of the substrate 4 and that the groove 12 extends so as to surround the center line CL of the pillar 11. In the SERS element 3 of the second embodiment, the fine structure part 7 is formed at a center part of the front face 4a of the substrate 4 and has a rectangular outer form on the order of several hundred µm×several hundred µm to several ten mm×several ten mm when seen in the thickness direction of the substrate 4. The pillars 11 of the fine structure part 7 are periodically arranged at a pitch on the order of several ten nm to several hundred nm (preferably 250 nm to 800 nm) along the front face 4a of the substrate 4.

The conductor layer 6 is formed over the fine structure part 7 and the front face 4a of the substrate 4. In the fine structure part 7, the conductor layer 6 reaches the exposed front face 4a of the substrate 4. In the SERS element 3, the conductor layer 6 formed on the fine structure part 7 and the front face 4a of the substrate 4 exposed at the fine structure part 7 constructs the optical function part 10 for generating surface-enhanced Raman scattering.

Figure 9:
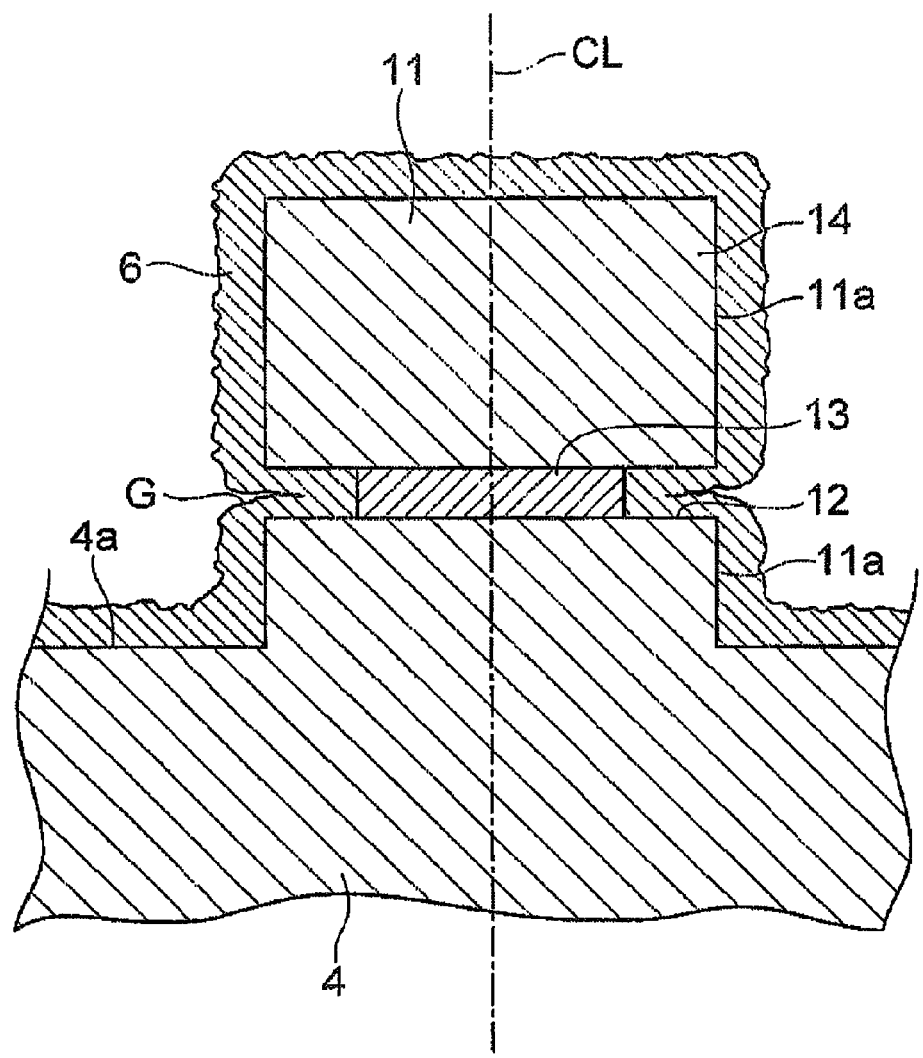
FIG. 9 is a vertical sectional view of a pillar and conductor layer in the optical function part of FIG. 8.

As illustrated in FIG. 9, one pillar 11 is provided with one groove 12 which extends like a circular ring so as to surround the center line CL of the pillar 11. The conductor layer 6 is formed on the outer surfaces of the pillars 11 and enters the groove 12 in the side face 11a of each pillar 11. As a consequence, the conductor layer 6 constituting the optical function part 10 is formed with the gap G along each groove 12. One pillar 11 may be provided with a plurality of grooves 12 juxtaposed along the center line CL, for example.

The SERS element 3 of the second embodiment constructed as in the foregoing also exhibits effects similar to those of the SERS element 3 of the above-mentioned first embodiment.

An example of methods for manufacturing the SERS element 3 of the second embodiment will now be explained. First, as illustrated in (a) of FIG. 10, the silicon wafer 40 to become the substrate 4 is prepared. Subsequently, as illustrated in (b) of FIG. 10, a sacrificial layer 13 made of $SiO_2$ is formed on the front face 40a of the silicon wafer 40. Then, as illustrated in (c) of FIG. 10, a surface layer 14 made of polysilicon is formed on a front face 13a of the sacrificial layer 13.

Next, as illustrated in (a) of FIG. 11, a resist layer RL is formed on a front face 14a of the surface layer 14. The resist layer RL has a pattern formed by photoetching, electron beam lithography, nanoimprint lithography, or the like. The pattern of the resist layer RL corresponds to a plurality of fine structure parts 7 and masks parts corresponding to the pillars 11 for each fine structure part 7. Subsequently, as illustrated in (b) of FIG. 11, dry etching using the resist layer RL as a mask removes the surface layer 14, the sacrificial layer 13, and a surface layer of the silicon wafer 40 from the region not covered with the resist layer RL, and then the remaining resist layer RL is eliminated. Thereafter, as illustrated in (c) of FIG. 11, laterally-exposed surface layers of the sacrificial layer 13 are selectively removed by dry or wet etching with another etchant, so as to form grooves 12 on the side faces 11a of the pillars 11. This yields the silicon wafer 40 formed with a plurality of fine structure parts 7.

A similar production is possible with SOI wafers. The material for the pillars 11 is not limited to silicon, nor is that for the sacrificial layer 13 to $SiO_2$. The pillars 11 and sacrificial layer 13 may be made of any materials as long as the sacrificial layer 13 can selectively be etched with respect to the pillars 11. It is not necessary for the substrate 4 and the leading end parts of the pillars 11 to be made of the same material. For example, the substrate 4 may be a silicone wafer, the sacrificial layer may be $SiO_2$, and the leading end parts of the pillars 11 may be a resin. The leading end parts of the pillars 11 may be formed by nanoimprinting when they are made of a resin.

Next, a film of a metal such as Au or Ag is produced on the molded layer 5 by vapor deposition such as resistance heating vapor deposition and electron beam vapor deposition or sputtering, so as to form the conductor layer 6. At this time, the conductor layer 6 enters the grooves 12 provided in the side faces 11a of the pillars 11 in the fine structure part 7, thereby forming the gaps G in the conductor layer 6 constituting the optical function part 10. Subsequently, the silicone wafer 40 is cut for each fine structure part 7 (i.e., for each optical function part 10), whereby a plurality of SERS elements 3 are obtained. For yielding the SERS unit 1, it is sufficient for the SERS element 3 manufactured as mentioned above to be attached onto the handling board 2.

As explained in the foregoing, the method for manufacturing the SERS element 3 in accordance with the second embodiment forms a plurality of gaps G in the conductor layer 6 by utilizing the grooves 12 provided in the side face 11a of each pillar 11. This can yield the gaps G, which favorably function as nanogaps, more stably than in the case of forming the gaps G at root parts of the pillars 11 where the forming condition of the conductor layer 6 is hard to stabilize.

Simply adjusting the thickness and position of the sacrificial layer 13 can easily change the width of the grooves 12, while just regulating the etching condition for the surface layer of the sacrificial layer 13 can readily alter the depth of the grooves 12, whereby the SERS element 3 formed with favorable nanogaps which can increase the intensity of surface-enhanced Raman scattering can be manufactured with a favorable yield.

Third Embodiment

Figure 12:
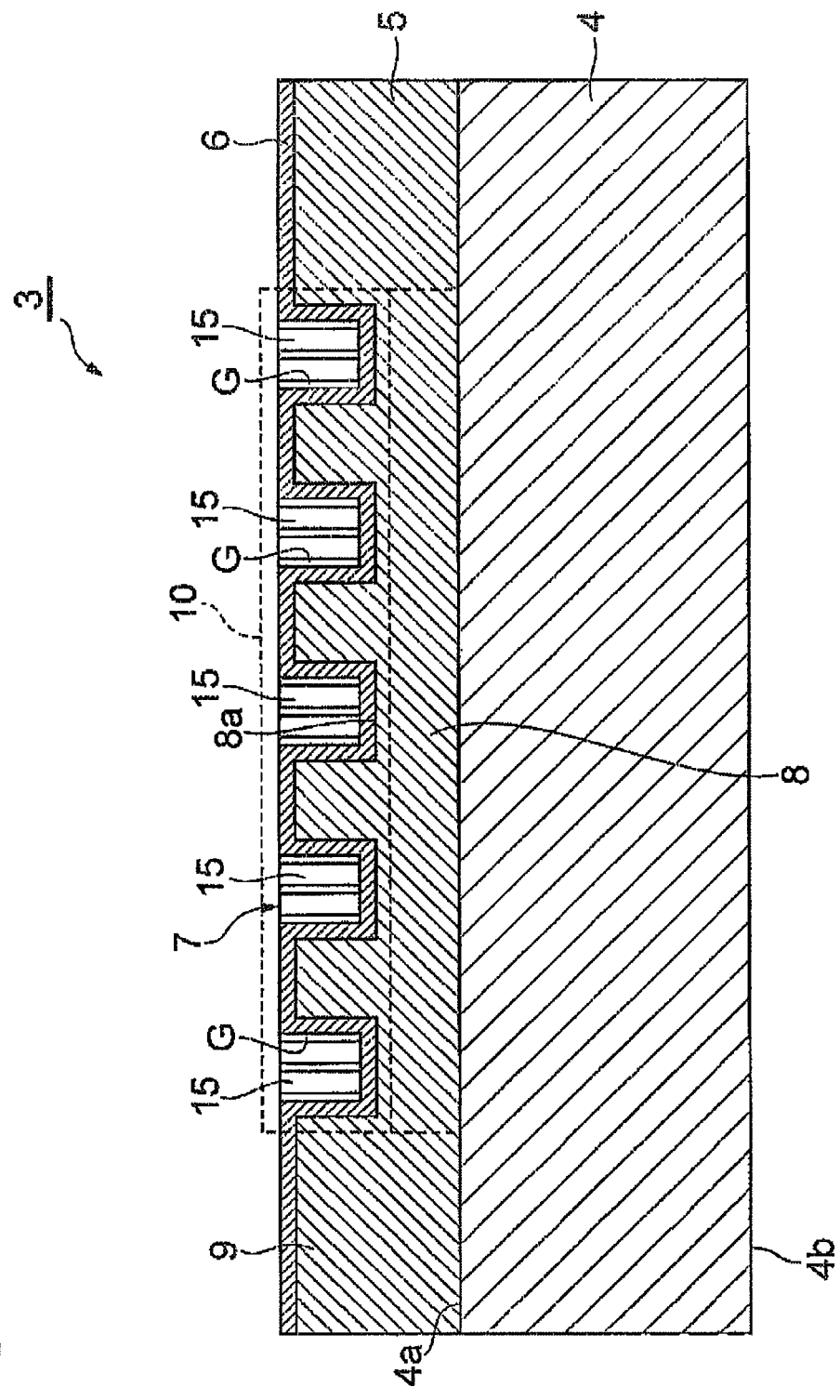
FIG. 12 is a vertical sectional view of the optical function part in the surface-enhanced Raman scattering element in accordance with a third embodiment of the present invention.

As illustrated in FIG. 12, the SERS element 3 of the third embodiment differs from the SERS element 3 of the above-mentioned first embodiment mainly in that holes (depressions) 15 are formed in the molded layer 5 instead of the pillars 11. In the SERS element 3 of the third embodiment, the fine structure part 7 is formed with a plurality of cylindrical holes, each having a diameter and depth on the order of several ten nm to several hundred nm, periodically arranged at a pitch on the order of several ten nm to several hundred nm (preferably 250 nm to 800 nm) along the front face 4a of the substrate 4.

The conductor layer 6 is formed over the fine structure part 7 and frame part 9. In the fine structure part 7, the conductor layer 6 reaches the surface 8a of the support part 8 (i.e., the bottom face of each hole 15) exposed to the side opposite from the substrate 4. In the SERS element 3, the conductor layer 6 formed on the fine structure part 7 and the surface 8a of the support part 8 constructs the optical function part 10 for generating surface-enhanced Raman scattering.

Figure 13:
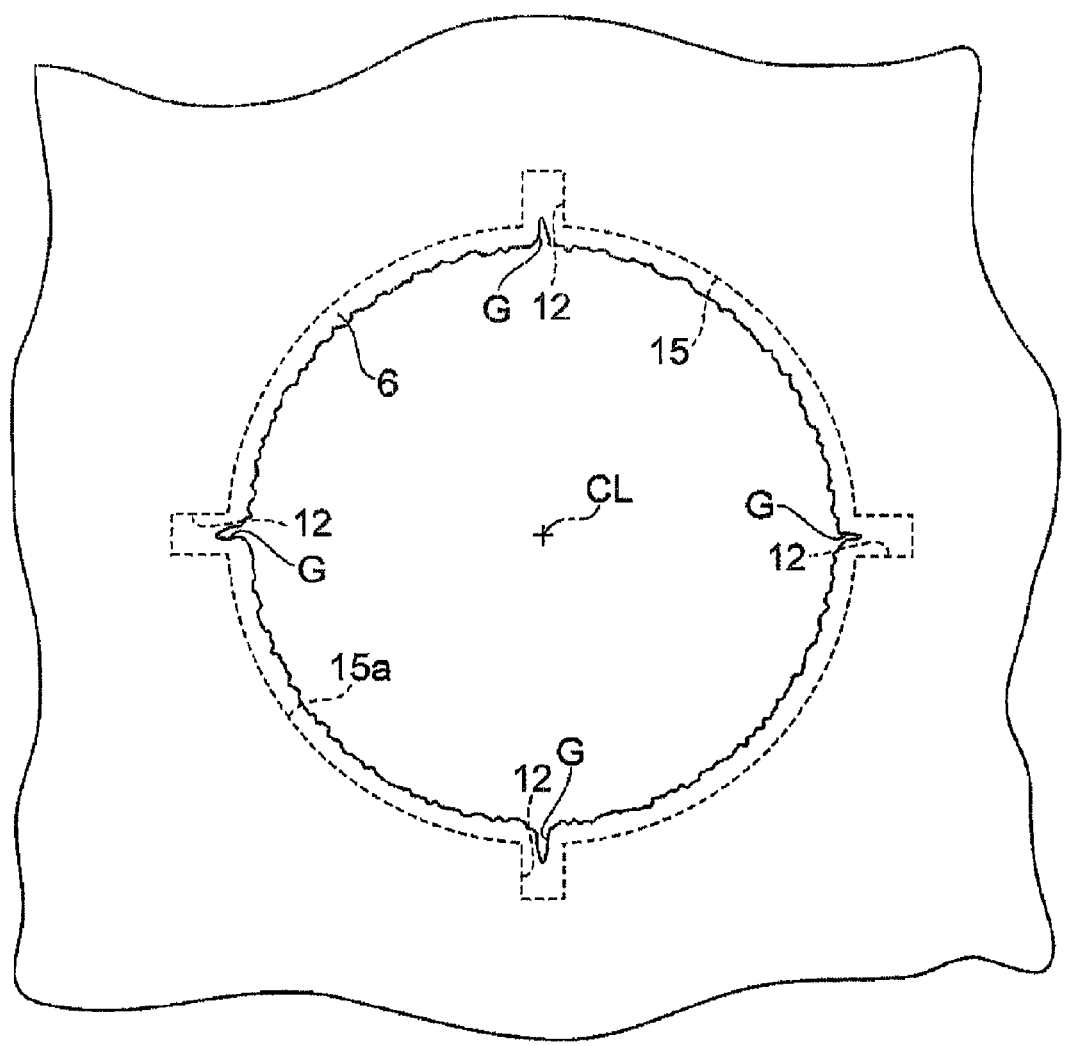
FIG. 13 is a plan view of a hole and conductor layer in the optical function part of FIG. 12.
Figure 14:
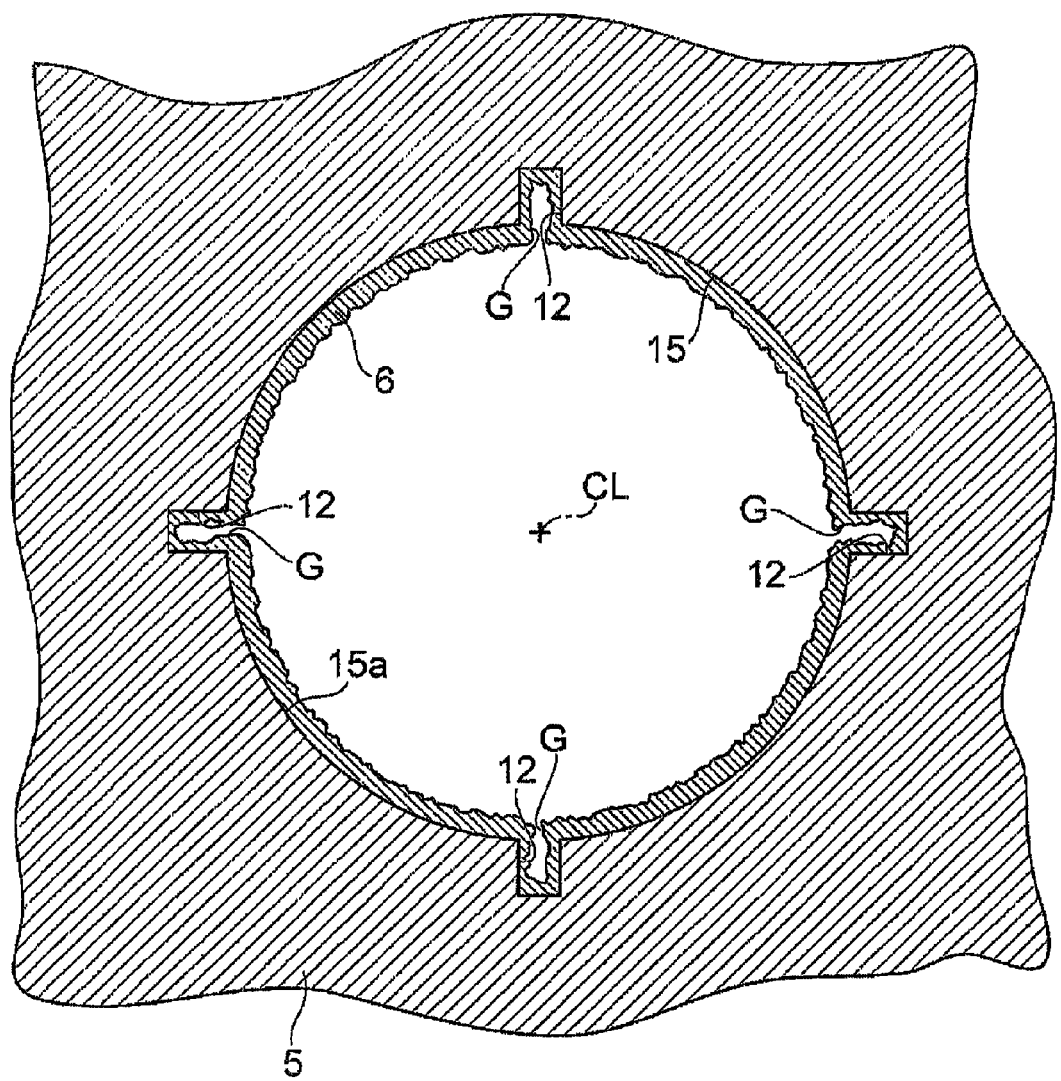
FIG. 14 is a horizontal sectional view of the hole and conductor layer in the optical function part of FIG. 12.

As illustrated in FIGS. 13 and 14, each hole 15 has a side face (inner surface) 15a provided with grooves 12, each of which has a rectangular cross section. One hole 15 is provided with a plurality of grooves 12 (four grooves at intervals of 90 degrees about the center line CL of the hole 15 in the SERS element 3 of the third embodiment), each of which extends along the center line CL. The conductor layer 6 is formed on the inner surfaces of the holes 15 and enters the respective grooves 12 in the side face 15a of each hole 15. As a consequence, the conductor layer 6, which constitutes the optical function part 10, is formed with gaps G along the respective grooves 12. The center line CL of the hole 15 is a line passing through the respective centers of gravity in cross-sectional forms of the hole 15 which are perpendicular to the center line CL.

In the SERS element 3 of the third embodiment constructed as in the foregoing, the conductor layer 6 enters the grooves 12 provided in the side faces 15a of the holes 15 in the fine structure part 7, thereby forming a plurality of gaps G in the conductor layer 6 constituting the optical function part 10. The gaps G formed in the conductor layer 6 favorably function as nanogaps where electric fields are locally enhanced. Therefore, the SERS element 3 of the third embodiment can increase the intensity of surface-enhanced Raman scattering by favorable nanogaps.

Since a plurality of holes 15 are periodically arranged along the front face 4a of the substrate 4, the intensity of surface-enhanced Raman scattering can be increased stably.

Since one hole 15 is provided with a plurality of grooves 12, the gaps G favorably functioning as nanogaps can be increased.

The fine structure part 7 can be formed in the molded layer 5 by nanoimprinting in the SERS element 3 of the third embodiment as in the SERS element 3 of the above-mentioned first embodiment. The fine structure part 7 may also be formed on the substrate 4 by etching with a mask having a pattern of a two-dimensional form (whose masking and opening parts are reversed from those of the mask in the above-mentioned first embodiment).

Fourth Embodiment

Figure 15:
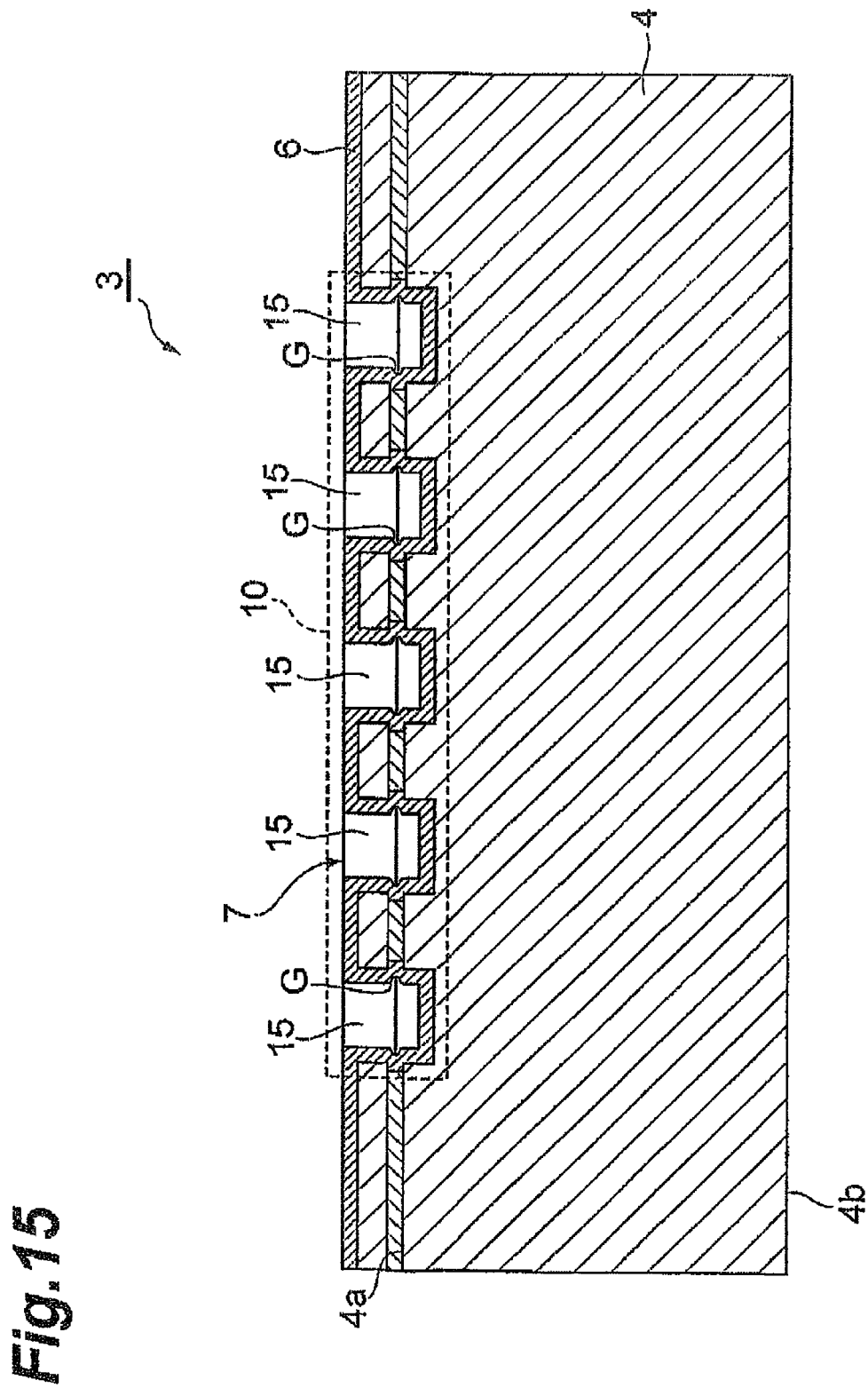
FIG. 15 is a vertical sectional view of the optical function part in the surface-enhanced Raman scattering element in accordance with a fourth embodiment of the present invention.

As illustrated in FIG. 15, the SERS element 3 of the fourth embodiment differs from the SERS element 3 of the above-mentioned third embodiment mainly in that the fine structure part 7 is formed in the front face 4a of the substrate 4 and that the groove 12 extends so as to surround the center line CL of the hole 15. In the SERS element 3 of the fourth embodiment, the fine structure part 7 is formed at a center part of the front face 4a of the substrate 4 and has a rectangular outer form on the order of several hundred μm×several hundred μm to several ten mm×several ten mm when seen in the thickness direction of the substrate 4. The holes 15 of the fine structure part 7 are periodically arranged at a pitch on the order of several ten nm to several hundred nm (preferably 250 nm to 800 nm) along the front face 4a of the substrate 4.

The conductor layer 6 is formed over the fine structure part 7 and the front face 4a of the substrate 4. In the fine structure part 7, the conductor layer 6 reaches the exposed front face 4a of the substrate 4 (i.e., the bottom face of each hole 15). In the SERS element 3, the conductor layer 6 formed on the fine structure part 7 and the front face of the substrate 4 exposed at the fine structure part 7 constructs the optical function part 10 for generating surface-enhanced Raman scattering.

Figure 16:
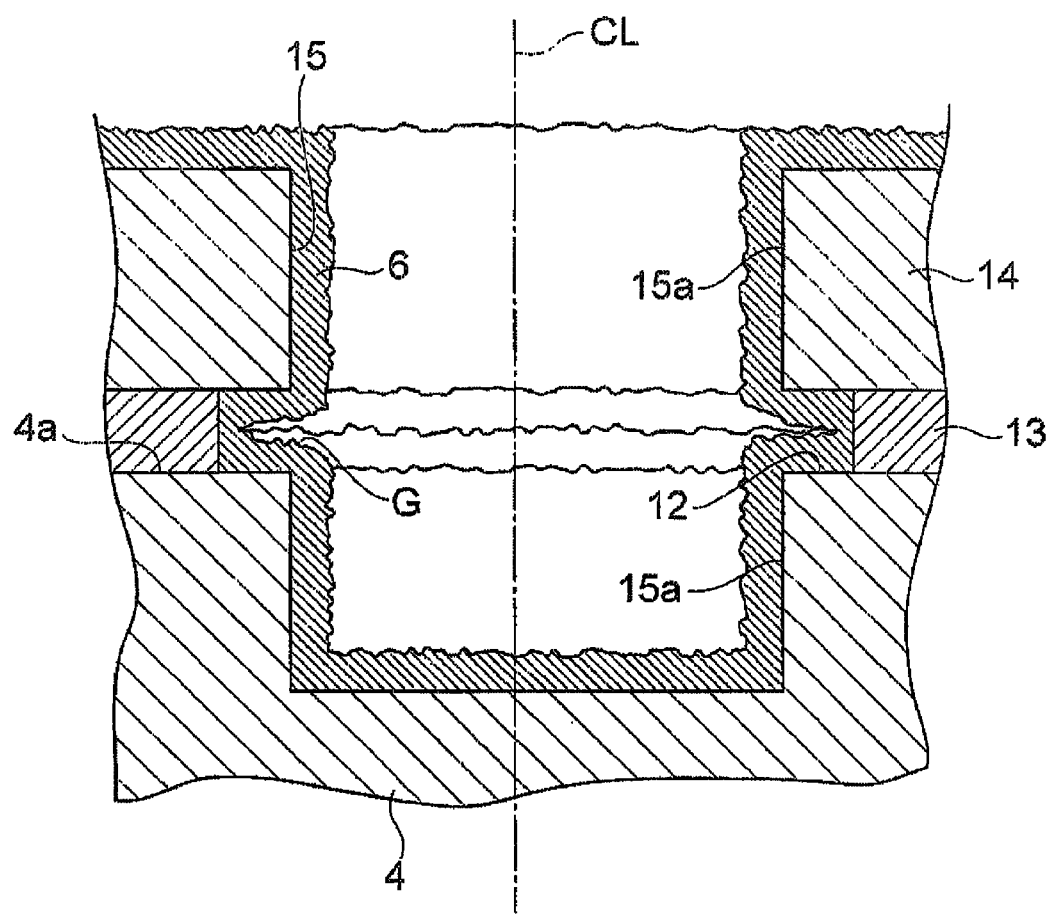
FIG. 16 is a vertical sectional view of a hole and conductor layer in the optical function part of FIG. 15.

As illustrated in FIG. 16, one hole 15 is provided with one groove 12 which extends like a circular ring so as to surround the center line CL of the hole 15. The conductor layer 6 is formed on the inner surfaces of the holes 15 and enters the groove 12 in the side face 15a of each hole 15. As a consequence, the conductor layer 6 constituting the optical function part 10 is formed with the gap G along each groove 12. One hole 15 may be provided with a plurality of grooves 12 juxtaposed along the center line CL, for example.

The SERS element 3 of the fourth embodiment constructed as in the foregoing also exhibits effects similar to those of the SERS element 3 of the above-mentioned third embodiment. The fine structure part 7 may also be formed on the substrate 4 by etching with a mask having a pattern of a two-dimensional form (whose masking and opening parts are reversed from those of the mask in the above-mentioned second embodiment) in the SERS element 3 of the fourth embodiment as in the SERS element 3 of the above-mentioned second embodiment.

While the first to fourth embodiments of the present invention are explained in the foregoing, the present invention is not limited to the above-mentioned embodiments. For example, the pillars 11 and holes 15 may be arranged one-dimensionally instead of two-dimensionally or in a triangular lattice instead of a square lattice. The cross-sectional form of the pillars 11 and holes 15 is not limited to circles, but may be ellipses or polygons such as triangles and quadrangles. Thus, without being restricted to those mentioned above, various materials and forms can be employed for constituents of the SERS element 3 and SERS unit 1.

The fine structure part 7 may be formed on the front face 4a of the substrate 4 either indirectly with the support part 8, for example, interposed therebetween as in the first and third embodiments or directly as in the second and fourth embodiments. The conductor layer 6 is not limited to the one directly formed on the fine structure part 7, but may be formed indirectly on the fine structure part 7 with a layer such as a buffer metal (Ti, Cr, or the like) for improving the adhesion of a metal to the fine structure part 7, for example, interposed therebetween.

Figure 17:
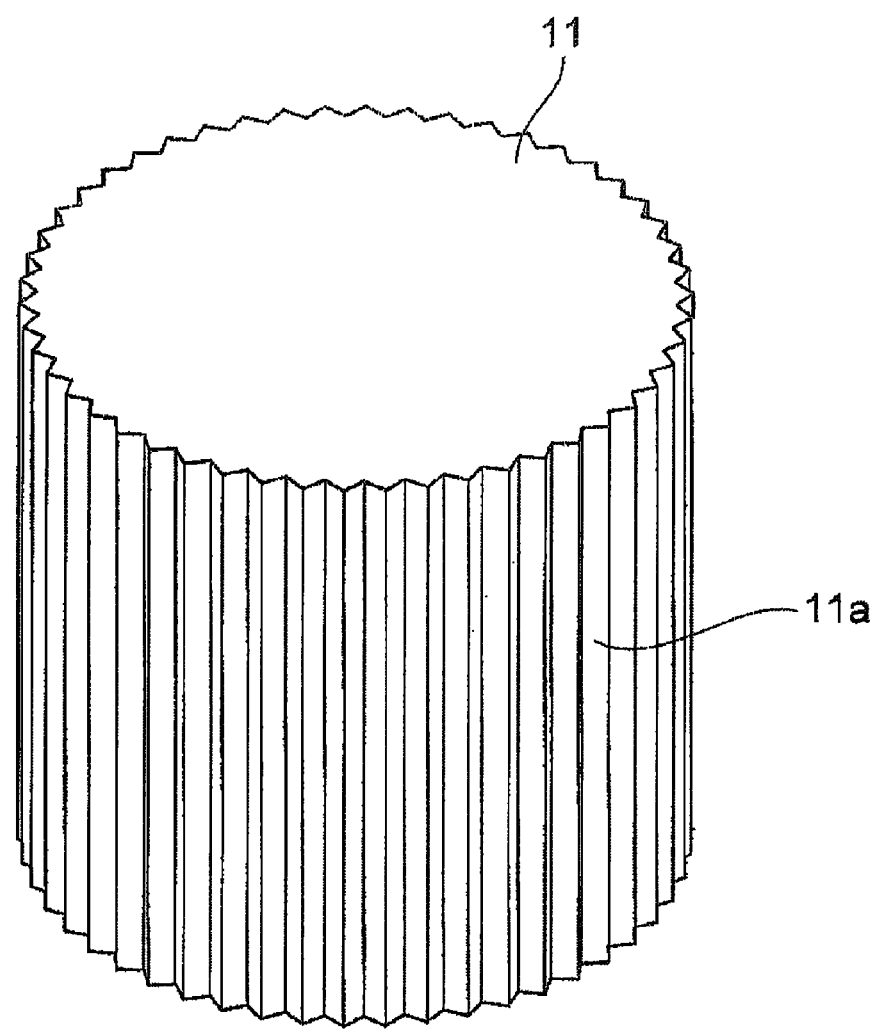
FIG. 17 is a modified example of the pillar in the optical function part of FIG. 3.
Figure 18:
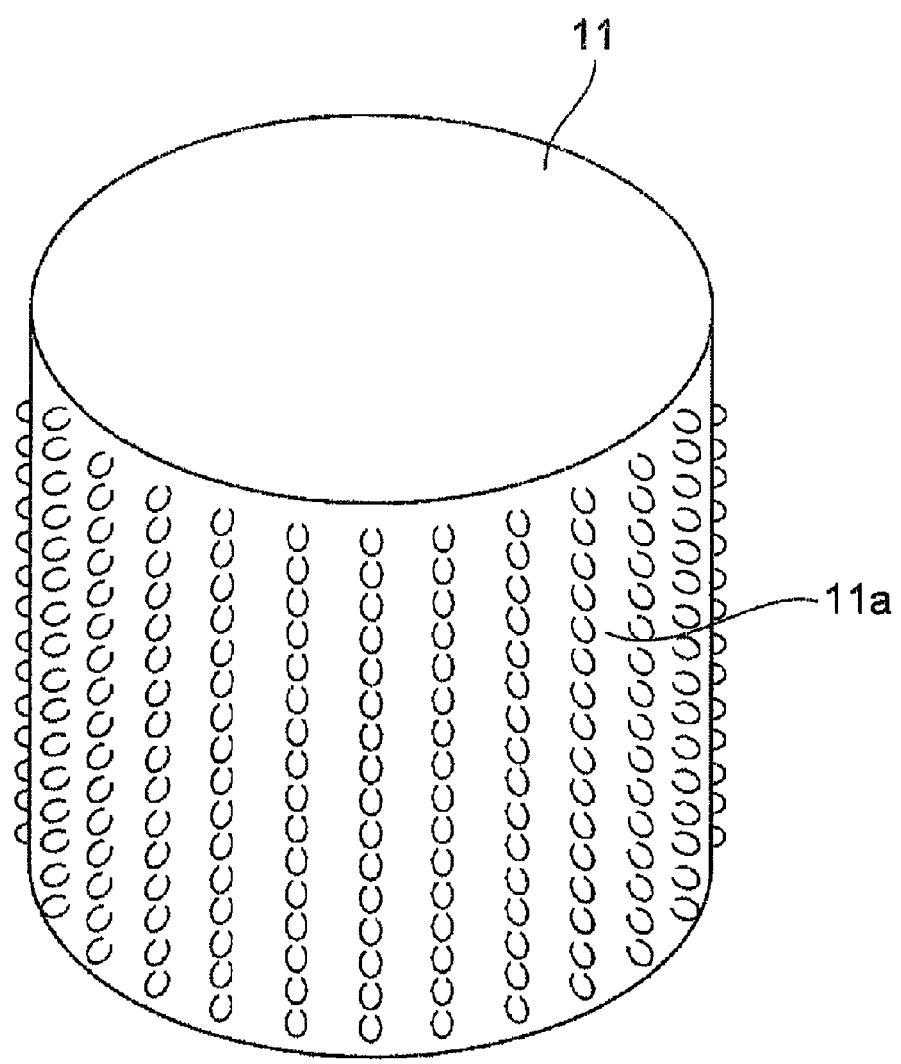
FIG. 18 is a modified example of the pillar in the optical function part of FIG. 3.

The cross-sectional form of the grooves 12 is not limited to rectangles, but may also be shaped like U, V, and the like. The conductor layer 6 may be either continuous or discontinuous within the groove 12 as long as it enters the groove 12 so as to form the gap G. The surfaces of the support part 8 and substrate 4 may be free of the conductor layer 6 (the conductor layer 6 may be formed only on the pillars 11 having the grooves 12 but discontinuous on the surfaces of the support part 8 and substrate 4) as long as the conductor layer 6 enters the groove 12 so as to form the gap G. Recessed regions other than the grooves 12 may also be provided in the outer surfaces of projections such as the pillars 11 and inner surfaces of depressions such as the holes 15. That is, the form of recessed regions serving as indentations is not limited as long as the conductor layer 6 forms the gap G by entering recessed regions such as cutouts and caves (dented regions, concave regions, and sunken regions) formed in the outer surfaces of projections and inner surfaces of depressions. By way of example, when mountains and valleys are repeatedly formed in the side face 11a of the pillar 11 as illustrated in FIG. 17, the valley parts become recessed regions. When mountains and valleys are repeatedly formed in the side face 15a of the hole 15, the valley parts similarly become recessed regions. When a number of protrusions are formed on the side face 11a of the pillar 11 as illustrated in FIG. 18, parts between the protrusions adjacent to each other become the recessed regions. When a number of protrusions are formed on the side face 15a of the hole 15, parts between the protrusions adjacent to each other similarly become the recessed regions.

When attention is focused on a pair of projections (those corresponding to the pillars 11) adjacent to each other, the width of the gap formed by the conductor layer entering a recessed region provided in the outer surface of the projection is smaller than the distance between the conductor layer formed on the outer surface of one projection and that formed on the outer surface of the other projection. This can easily and stably form such a narrow gap (gap favorably functioning as a nanogap) as to be unattainable by the configuration of the fine structure part alone.

Figure 19:
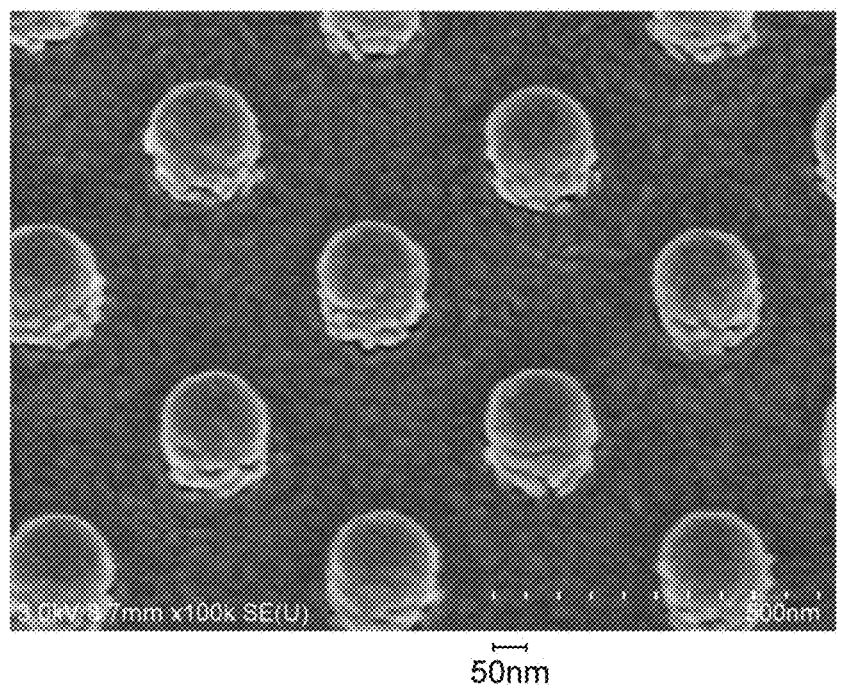
FIG. 19 is a SEM photograph of an optical function part in a surface-enhanced Raman scattering element.

For reference, a SEM photograph of an optical function part of a surface-enhanced Raman scattering element will be explained. The optical function part shown in FIG. 19 is one in which Au was vapor-deposited as a conductor layer so as to yield a thickness of 50 nm in a fine structure part made of a nanoimprinting resin having a plurality of pillars (each having a diameter of 120 nm and a height of 180 nm) periodically arranged at a predetermined pitch (center line distance of 360 nm).

INDUSTRIAL APPLICABILITY

The present invention can provide a surface-enhanced Raman scattering element which can increase the intensity of surface-enhanced Raman scattering by a favorable nanogap.

REFERENCE SIGNS LIST

3: SERS element (surface-enhanced Raman scattering element); 4: substrate; 4a: front face (principal surface); 6: conductor layer; 7: fine structure part; 10: optical function part; 11: pillar (projection); 11a: side face (outer surface); 12: groove (recessed region); 15: hole (depression); 15a: side face (inner surface); G: gap; CL: center line.

The invention claimed is:

1. A surface-enhanced Raman scattering element comprising:
   a substrate having a principal surface;
   a fine structure part formed on the principal surface and having a plurality of projections; and
   a conductor layer formed on the fine structure part and constituting an optical function part for generating surface-enhanced Raman scattering;
   wherein the projections have respective outer surfaces provided with recessed regions;
   wherein a plurality of gaps are formed in the conductor layer by entering the recessed regions; and
   wherein, when attention is focused on a pair of projections adjacent to each other, a width of the gap formed by the conductor layer entering a recessed region provided in the outer surface of a projection is smaller than a distance between the conductor layer formed on the outer surface of one projection and that formed on the outer surface of the other projection,
   the recessed region is formed in a region that is at least not a root part of the projection, and the root part of the projection includes a region that is not a recessed region.

2. A surface-enhanced Raman scattering element according to claim 1, wherein the projections are arranged periodically along the principal surface.

3. A surface-enhanced Raman scattering element according to claim 1, wherein one of the projections is provided with a plurality of the recessed regions.

4. A surface-enhanced Raman scattering element according to claim 1, wherein the recessed region is a groove extending along a center line of the projection.

5. A surface-enhanced Raman scattering element according to claim 1, wherein the recessed region is a groove extending so as to surround a center line of the projection.

6. A surface-enhanced Raman scattering element comprising:
   a substrate having a principal surface;
   a fine structure part formed on the principal surface and having a plurality of depressions; and
   a conductor layer formed on the fine structure part and constituting an optical function part for generating surface-enhanced Raman scattering;
   wherein the depressions have respective inner surfaces provided with recessed regions;
   wherein a plurality of gaps are formed in the conductor layer by entering the recessed regions; and
   wherein a width of the gap formed by the conductor layer entering a recessed region provided in the inner surface of a depression is smaller than an inner width of the conductor layer formed on the inner surface of the depression, and
   the depression is a hole, and the recessed region is disposed in a region of an inner surface of the hole spaced apart from a bottom face of the hole.

7. A surface-enhanced Raman scattering element according to claim 6, wherein the depressions are arranged periodically along the principal surface.

8. A surface-enhanced Raman scattering element according to claim 6, wherein one of the depressions is provided with a plurality of the recessed regions.

9. A surface-enhanced Raman scattering element according to claim 6, wherein the recessed region is a groove extending along a center line of the depression.

10. A surface-enhanced Raman scattering element according to claim 6, wherein the recessed region is a groove extending so as to surround a center line of the depression.

* * * * *